(12) United States Patent
Van Damme et al.

(10) Patent No.: US 8,476,076 B2
(45) Date of Patent: *Jul. 2, 2013

(54) CHROMATOGRAPHY OF POLYOLEFIN POLYMERS

(75) Inventors: Freddy A. Van Damme, Brugge (BE); John W. Lyons, Midland, MI (US); William L. Winniford, Lake Jackson, TX (US); Alexander Willem deGroot, Sugar Land, TX (US); Matthew D. Miller, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/289,444

(22) Filed: Nov. 4, 2011

(65) Prior Publication Data

US 2012/0047990 A1     Mar. 1, 2012

Related U.S. Application Data

(63) Continuation of application No. 12/572,313, filed as application No. PCT/US2009/059261 on Oct. 1, 2009, now Pat. No. 8,076,147.

(60) Provisional application No. 61/195,326, filed on Oct. 6, 2008, provisional application No. 61/181,015, filed on May 26, 2009.

(51) Int. Cl.
| | | |
|---|---|---|
| *G01N 33/44* | (2006.01) | |
| *G01N 30/02* | (2006.01) | |
| *C08F 6/06* | (2006.01) | |
| *C08F 210/06* | (2006.01) | |

(52) U.S. Cl.
USPC .......... 436/85; 436/161; 210/198.2; 210/656; 528/482

(58) Field of Classification Search
USPC ................ 528/482; 210/656, 198.2; 436/85, 436/161
See application file for complete search history.

(56) References Cited

U.S. PATENT DOCUMENTS

| | | | | |
|---|---|---|---|---|
| 5,008,204 | A * | 4/1991 | Stehling ........................ | 436/85 |
| 5,272,236 | A | 12/1993 | Lai et al. | |
| 5,278,272 | A | 1/1994 | Lai et al. | |
| 6,260,407 | B1 | 7/2001 | Petro et al. | |
| 6,345,528 | B2 | 2/2002 | Petro et al. | |
| 6,406,632 | B1 | 6/2002 | Safir et al. | |
| 6,584,832 | B2 | 7/2003 | Petro et al. | |
| 6,855,258 | B2 * | 2/2005 | Petro et al. ...................... | 506/12 |
| 7,078,164 | B1 | 7/2006 | Diamond et al. | |
| 7,214,320 | B1 * | 5/2007 | Gregori et al. ................ | 210/656 |
| 7,355,089 | B2 | 4/2008 | Chang et al. | |
| 8,076,147 | B2 | 12/2011 | Damme et al. | |
| 2002/0056686 | A1 * | 5/2002 | Kyrlidis et al. ............... | 210/656 |

FOREIGN PATENT DOCUMENTS

WO     01/98371 A3     12/2001

OTHER PUBLICATIONS

Takeuchi et al, "Ion Chromatography of Inorganic Anions on Graphitic Carbon as the Stationary Phase," J. High Resol. Chromatography 2000, 23, (10) 590-594.*
Marin et al, "Effect of high-temperature on high-performance liquid chromatography column stability and performance under temperature-programmed conditions," Journal of Chromatography A, 1030 (2004) 255-262.*
Macko, T.; Pasch, H.; Denayer, JF. J. Chromatog. A 2003, 1002 55.
Macko, T.; Denayer, Jf.; Pasch, H.; Baron, GV. J. Sep. Sci 2003, 26, 1569.
Macko, T.; Pasch, H.; Denayer, JF. J. Sep. Sci 2005, 28, 59.
Wang, X.; Rusa, C.; Hunt, M.; Tonelli, A.; Macko T. Macromolecules 2005, 38, 10341.
Macko, T.; Pasch, H.; Milonjic, S.; Hiller, W. Chromatographia 2006, 64, 183.
Macko, T.; Pasch, H.; Brüll, R. J. Chromatog. A 2006, 1115, 81.
Heinz, L.; Pasch, H. Polymer 2005, 46, 12040.
Findenegg, G.; Liphard, M. Carbon 1987, 25, 119.
Yin, S.; Wang, C.; Qiu, X.; Xu, B.; Bai, C. Surf. Interface Anal. 2001, 32, 248.
Hanai, T. J. Chromatog. A 2003, 989, 183.
Knox, J.; Ross, P. Carbon-based packing materials for liquid chromatography—Structure, performance, and retention mechanisms. In Advances in Chromatography. Brown, P.; Grushka, E., Eds.; Marcel Dekker, Inc.: New York, 1997; vol. 37, 73-120.
Ross, P.; Knox, J. Carbon-based packing materials for liquid chromatography—Applications. In Advances in Chromatography. Brown, P.; Grushka, E., Eds.; Marcel Dekker, Inc.: New York, 1997; vol. 37, 121-162.
Comparison of the retention behavior of polyethoxylated alcohols on porous graphitic carbon and polar as well as apolar bonded-silica phases. Chaimbault, P.; Elfakir, C.; Lafosse, M. UFR Sciences, CNRS UPRES A 6005, Institut de Chimie Organique et Analytique, Universite d'Orleans, BP 6759, Orleans Cedex 2, Fr. Journal of Chromatography, A (1998), 797(1+2), 83-91.
Journal of Liquid Chromatography (1991), 14, (13), 2477-98.
Albrecht, et al. Macromolecules, 2007, 40, 5545.
Albrecht, et al. Macromol. Symp. 2007, 257, 46.

(Continued)

*Primary Examiner* — Fred M Teskin

(57) ABSTRACT

A method and apparatus for chromatography of a polyolefin polymer by flowing a solution of the polyolefin polymer through liquid flowing through a graphitic carbon liquid chromatography stationary phase. The method can be used to determine the monomer to comonomer ratio of a polyolefin copolymer such as a copolymer of ethylene and 1-octene or a copolymer of propylene and ethylene.

17 Claims, 8 Drawing Sheets

OTHER PUBLICATIONS

Pereira, L; Aspey, S; Ritchie, H; "High temperature to increase throughput in liquid chromatography and liquid chromatography-mass spectrometry with a porous graphitic carbon stationary phase" Journal of Separation Science, vol. 30, No. 8, Apr. 12, 2007, pp. 1115-1124.

Sweeney, A. P; Wong, V; Shalliker, R. A; "The Seperation of diastereoisomers of polystyrene oligomers in reversed phase HPLC" Chromatographia, vol. 54, No. 1-2, Jul. 2001, pp. 24-30.

Marin, S. J, et al. "Effect of high-temperature on high-performance liquid chromatography column stability and performance under temperature-programmed conditions" Journal of Chromatography, Elsevier Science Publishers B. V, NL, vol. 1030, No. 1-2, Mar. 19, 2004, pp. 255-262.

Pasch, H; Heinz, L-C; Macko, T; Hiller, W, "High-Temperature gradient HPLC and LC-NMR for the analysis of complex polyolefins" Pure and Applied Chemistry, vol. 80, No. 8, Aug. 2008, pp. 1747-1762.

Miller, M, et al. "Separation of Polyolefins Based on Comonomer Content Using High-Temperature Gradient Adsorption Liquid Chromatography with a Graphitic Carbon Column" Journal of Applied Polymer Science, May 10, 2010.

PCT/US2009/059261, International Search Report, dated Apr. 13, 2011.

PCT/US2009/059261, International Preliminary Report on Patentability, dated Apr. 19, 2011.

PCT/US2009/059261, Written Opinion of the International Searching Authority, dated Apr. 13, 2011.

* cited by examiner

CHROMATOGRAPHY OF POLYOLEFIN POLYMERS

REFERENCE TO RELATED APPLICATIONS

This present application is a Continuation of U.S. application Ser. No. 12/572,313, filed Oct. 2, 2009, now U.S. Pat. No. 8,076,147, and which is a 35 U.S.C. §371 of International Application No. PCT/US09/059,261, filed Oct. 1, 2009, which claims the benefit of U.S. Provisional 61/195,326 filed on Oct. 6, 2008 and U.S. Provisional No. 61/181,015 filed on May 26, 2009, and fully incorporated herein by reference.

BACKGROUND OF THE INVENTION

The disclosed invention is in the field of liquid chromatography. Liquid chromatography is used by the art to analyze polymers with regard to molecular size by Size Exclusion Chromatography (SEC) and with regard to chemical composition by High Performance Liquid Chromatography (HPLC). This disclosure relates to HPLC analysis of polymers with regard to chemical composition.

Polyolefin polymers (such as polymers and copolymers comprising polymerized ethylene monomer and/or propylene monomer) have long been analyzed with regard to chemical composition distribution by temperature rising elution fractionation (TREF) and crystallization analysis fractionation (CRYSTAF). However, neither TREF nor CRYSTAF can be used to analyze amorphous polyolefin polymers. Furthermore, both TREF and CRYSTAF require a relatively long analysis time. Therefore, the art turned to HPLC in an attempt to reduce analysis time and to expand the scope of analysis to amorphous polymers. Macko et al. apparently were the first to do so in 2003 by studying the retention of polyethylene standards on silica and zeolite stationary phases (J. Chrom. A, 1002 (2003) 55). Wang, et al. studied the retention of polyethylene and polypropylene by zeolites in 2005 (Macromolecules, V. 38, No. 25 (2005) 10341). Heinz and Pasch used a silica stationary phase to analyze polyethylene—polypropylene blends by HPLC (Polymer 46 (2005) 12040). Albrecht, et al., used a silica stationary phase to analyze ethylene—vinyl acetate copolymers by HPLC (Macromolecules 2007, 40, 5545). Albrecht, et al., used a silica stationary phase to analyze ethylene—propylene copolymers by HPLC (Macromol. Symp. 2007, 257, 46). A remaining problem for the HPLC analysis of polyolefin polymers is the limited separation efficiency obtained by the prior art methods.

SUMMARY OF THE INVENTION

A primary benefit of this disclosure is the provision of an HPLC method having improved separation efficiency for the analysis of a polyolefin polymer. More specifically, in one embodiment this disclosure is a method for chromatography of a polyolefin polymer, comprising the step of: introducing a solution of the polyolefin polymer into a liquid mobile phase flowing through a liquid chromatography stationary phase, the liquid chromatography stationary phase comprising graphitic carbon, the polyolefin polymer emerging from the liquid chromatography stationary phase with a retention factor greater than zero.

In another embodiment, this disclosure is an improved liquid chromatography method comprising the step of introducing a solution of the polyolefin polymer into a liquid mobile phase flowing through a liquid chromatography stationary phase, the polyolefin polymer emerging from the liquid chromatography stationary phase with a retention factor greater than zero the improvement comprising the liquid chromatography stationary phase comprising graphitic carbon.

In another embodiment, this disclosure is a method for determining the monomer to comonomer ratio of a copolymer consisting essentially of ethylene and an alpha olefin comonomer, comprising the steps of: (a) flowing a liquid mobile phase into contact with a liquid chromatography stationary phase comprising graphitic carbon to produce an effluent stream of liquid mobile phase from the stationary phase; (b) introducing a solution of the copolymer into the liquid mobile phase so that the copolymer emerges in the effluent stream with a retention factor that varies as a mathematical function of the monomer to comonomer ratio of the copolymer.

In another embodiment, this disclosure is a method for determining the monomer to comonomer ratio of a copolymer consisting essentially of propylene and an alpha olefin comonomer, comprising the steps of: (a) flowing a liquid mobile phase into contact with a liquid chromatography stationary phase comprising graphitic carbon to produce an effluent stream of liquid mobile phase from the stationary phase; (b) introducing a solution of the copolymer into the liquid mobile phase so that the copolymer emerges in the effluent stream with a retention factor that varies as a mathematical function of the monomer to comonomer ratio of the copolymer.

In another embodiment, this disclosure is an improved chromatographic fractionation technique for separating atactic and isotactic polypropylene from syndiotactic polypropylene.

In yet another embodiment, the invention is an apparatus for determining the monomer to comonomer ratio of a copolymer, especially a copolymer of ethylene or propylene and at least one C3-C20 alpha-olefin. The apparatus comprises a high temperature liquid chromatography unit (e.g., a WATERS GPCV2000 or a Polymer Laboratories 210 or 220 equipped with a graphitic carbon liquid chromatography column (such as HYPERCARB brand) and a pump.

In another embodiment, the invention is a method of establishing and/or maintaining quality control of a polymerization product, such as an ethylene based polymer or a propylene based polymer.

In still another embodiment, the invention is a method of removing molecular components having a specific comonomer content in a commercial polymerization process for polyolefin production to produce a product with a narrower comonomer distribution.

DETAILED DESCRIPTION

Figure 1:
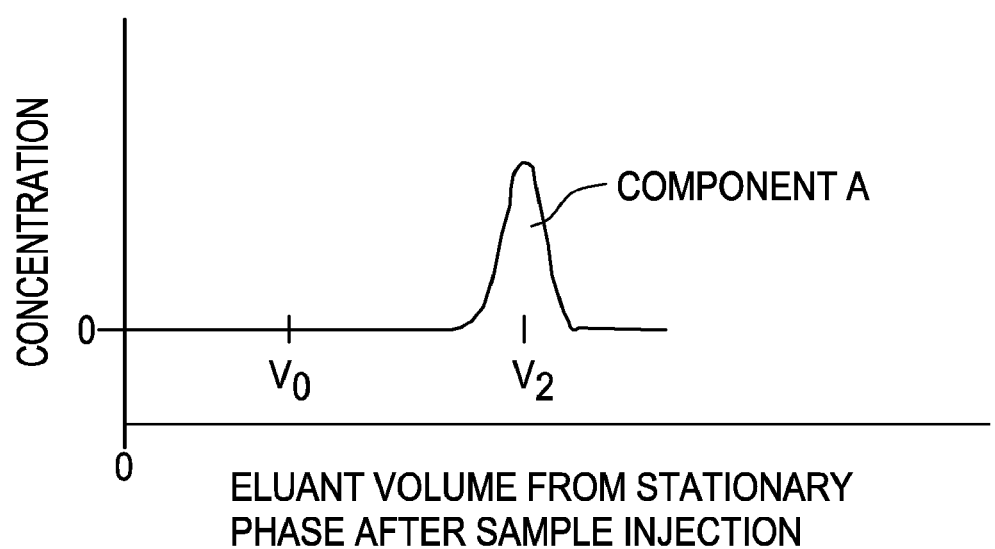
FIG. 1 is a theorized HPLC chromatogram depicting the elution of a retained component.

The theorized HPLC chromatogram shown in FIG. 1 depicts the elution of COMPONENT A at an elution volume peaking at Vr. A low molecular weight unretained component eluting from the stationary phase would elute at $V_0$. The retention factor (k) for COMPONENT A is $(Vr-V_0) \div V_0$.

Figure 2:
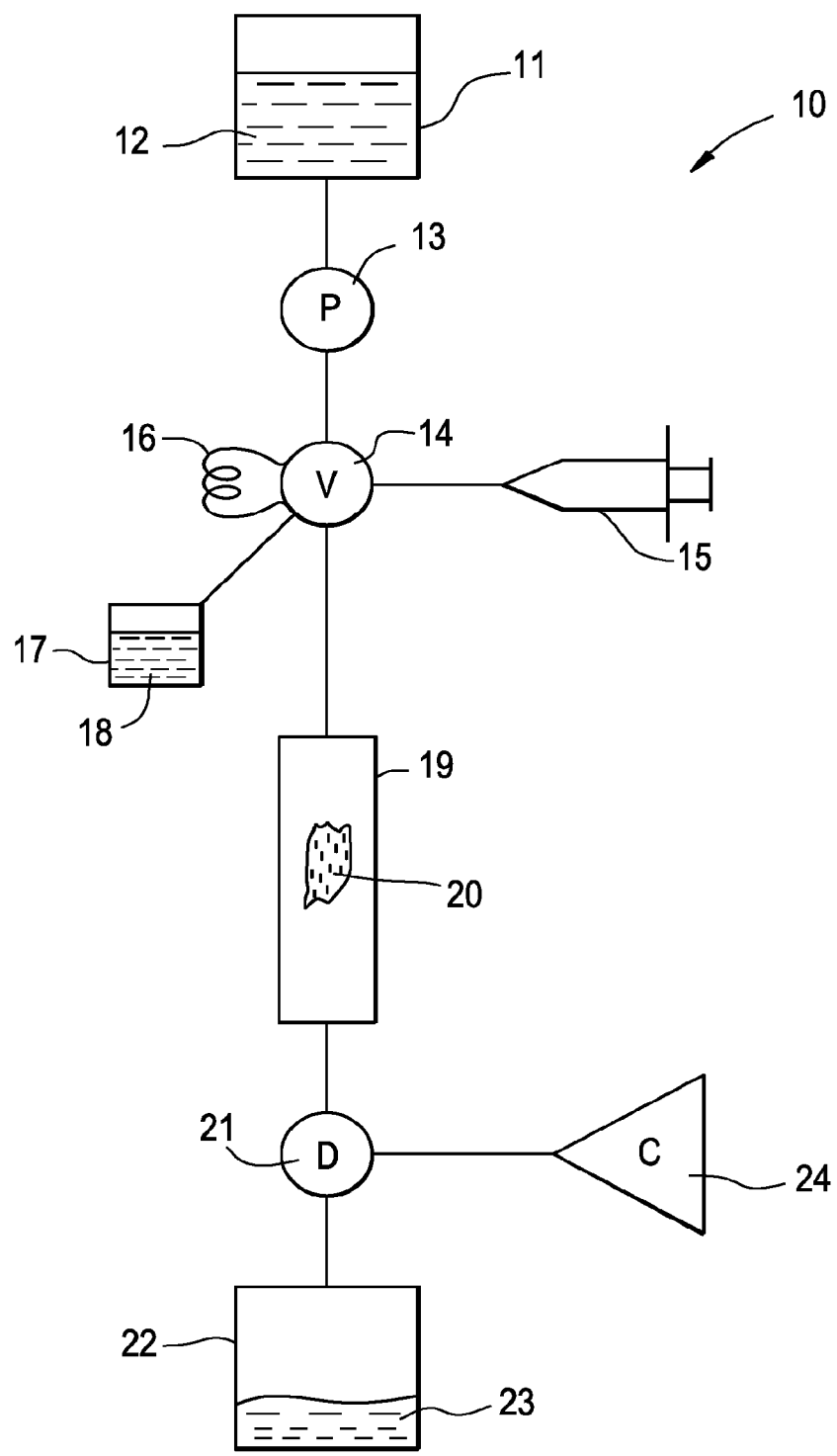
FIG. 2 shows a typical HPLC system.

FIG. 2 shows a typical HPLC system 10 of the prior art that includes an eluant reservoir 11 filled with a liquid mobile phase 12 or when a gradient system is used multiple reservoirs would be needed. The liquid mobile phase 12 is pumped by pump 13 through injection valve 14 into chromatography column 19. The chromatography column 19 is filled with liquid chromatography stationary phase 20 comprised in a granular packing. The liquid mobile phase 12 flows through the liquid chromatography stationary phase 20, through detector 21 and into used eluant reservoir 22 as used liquid mobile phase 23. A solution of a sample to be analyzed is contained in syringe 15 and dispensed through sample volume loop 16 of injection valve 14 in its sample load position into excess sample reservoir 17 as excess sample 18. When injection valve 14 is placed in its sample inject position, liquid mobile phase 12 is flowed through the sample volume loop 16 to flow the injected sample into the chromatography column 19. If a component of the injected sample is retained by the stationary phase 20 so that the component flows through the chromatography column 19 at a slower rate than the mobile phase 12, then the component will emerge from the chromatography column 19 with a retention factor greater than zero to be detected by detector 21. A general purpose digital computer 24 is in electrical communication with detector 21 and is programmed to manipulate the signal from the detector 21 to provide, for example, a chromatogram of the injected sample.

This disclosure is a method for chromatography of a polyolefin polymer, comprising the step of: introducing a solution of the polyolefin polymer into a liquid flowing through a liquid chromatography stationary phase, the liquid chromatography stationary phase comprising graphitic carbon, the polyolefin polymer emerging from the liquid chromatography stationary phase with a retention factor greater than zero. The improvement of this disclosure centers on the use of a liquid chromatography stationary phase comprising graphitic carbon.

This disclosure is also a method for determining the monomer to comonomer ratio of a copolymer consisting essentially of ethylene or propylene and an alpha olefin comonomer, comprising the steps of: (a) flowing a liquid mobile phase into contact with a liquid chromatography stationary phase comprising graphitic carbon to produce an effluent stream of liquid mobile phase from the stationary phase; (b) introducing a solution of the copolymer into the liquid mobile phase so that the copolymer emerges in the effluent stream with a retention factor that varies as a mathematical function of the monomer to comonomer ratio of the copolymer.

The term "polyolefin polymer" in this disclosure is defined as all polymers and copolymers (including high pressure low density polyethylene (LDPE), heterogeneous polymers, random, block, and graft polymers, interpolymers and copolymers) comprising one or more polymerized monomers selected from the group consisting of ethylene, an alpha olefin having from 3-20 carbon atoms (such as 1-propylene, 1-butene, 1-hexene, 1-heptene and 1-octene), 4-methyl-1-pentene, and/or acetylenically unsaturated monomers having from 2-20 carbons, and/or diolefins having from 4-18 carbons and any other monomer used in the art to modify the density of a polymer. Heterogeneous polymers include Ziegler-Natta polymerized polymers such as LLDPE and HDPE and include products such as DOWLEX™ made by The Dow Chemical Company. The random copolymers include those polymerized using metallocene or constrained geometry catalyst technology and include polymers such as AFFINITY™ and ENGAGE™, both available from The Dow Chemical Company, and EXACT™, available from ExxonMobil. Methods for polymerizing these random copolymers are well known in the art and include those described in U.S. Pat. Nos. 5,272,236 and 5,278,272. The block coplymers include those polymerized using chain shuttling technology and two catalyst species, such as is disclosed in U.S. Pat. No. 7,355,089, and include polymers such as INFUSE™ Olefin Block Copolymers made by The Dow Chemical Company. In addition the term "polyolefin polymer" in this disclosure is defined as a polymer having an average molecular weight, as determined by light scattering, greater than 1,000 grams per mole (preferably greater than 2,000 grams per mole and more preferably greater than 4,000 grams per mole). The polyolefin polymer can be a copolymer consisting essentially of polymerized ethylene monomer and a polymerized alpha olefin monomer such as 1-octene. The polyolefin polymer can be a copolymer consisting essentially of polymerized propylene monomer and a polymerized alpha olefin monomer such as ethylene. Such propylene based polymers include homopolymer polypropylene, impact propylene based copolymers, and random propylene based copolymers. Other more specialized polymers also benefit from the method and apparatus disclosed herein and include ethylene/acrylic acid copolymers, ethylene/vinyl acetate copolymers and ethylene/styrene interpolymers, halogenated polymers, and polymers containing maleic anhydride moeities.

In most applications the temperature of the solution of the polyolefin polymer, the temperature of the liquid chromatography stationary phase and the temperature of the detector will be controlled at an elevated temperature to increase the solubility of the polyolefin polymer, e.g., to render the polyolefin polymer soluble. The concentration of the polyolefin polymer in the solution of polyolefin polymer is preferably greater than 0.1 milligrams per milliliter of solution, especially greater than 2 mg/mL. The solvent used for the solution of the polyolefin polymer is preferably decanol when the polyolefin polymer is polyethylene or polypropylene. Any suitable liquid mobile phase can be used in the method of this disclosure. A gradient composition mobile phase is preferred in the method of this disclosure. The temperature of the liquid chromatography stationary phase can be increased during the method of this disclosure. A mobile phase having no aliphatic hydrogen content (such as 1,2,4-trichloro benzene) facilitates the use of an infrared detector for the method of this disclosure.

Any liquid chromatography stationary phase that comprises graphitic carbon can be used in the method of this disclosure. The term "graphitic carbon" in this disclosure is defined as all varieties of materials comprising the element carbon in the allotropic form of graphite irrespective of the presence of structural defects if the three-dimensional hexagonal crystalline long-range order of graphite can be detected in the material by diffraction methods (such as X-ray diffraction spectroscopy) independent of the volume fraction and the homogeneity of distribution of such crystalline domains. Carbon nanotubes and carbon "buckyballs" are examples of forms of graphitic carbon that are useful in the method of this disclosure. Preferably, the liquid chromatography stationary phase consists essentially of graphitic carbon, especially porous graphitic carbon. The graphitic carbon is usually packed into columns and comprises flat sheets of hexagonally arranged carbon atoms at the molecular level. The graphitic carbon desirably has a particle size of from about 1 to about 10 microns, preferably an average particle size of about 3 microns, or 5 microns or 7 microns, and preferably has an average pore size of about 200 to about 300 Angstroms, more preferably an average pore size of about 250 Angstroms. The internal surface of the graphitic carbon has an area of about 100 to about 140 square meters/gram, preferably about 120 square meters/gram. The length of the columns is typically from about 30 mm to about 100 mm and can have a diameter of from about 2 mm to about 5 mm. An example of a commercially available liquid chromatography stationary phase that consists essentially of graphitic carbon is believed to include the HYPERCARB brand HPLC column from Thermo Scientific, Waltham Mass. An example of a commercially available liquid chromatography stationary phase that comprises graphitic carbon is believed include the DISCOVERY ZR-CARBON brand HPLC column from Sigma Aldrich, St. Louis, Mo. Leboda, et al, Materials Chemistry and Physics 55 (1998) pages 1-29, is a literature review of HPLC carbon adsorbents.

The method of this disclosure can be coupled, on or off line, with other analytical methods. For example, the effluent from an SEC column containing an ethylene 1-octene polyolefin copolymer of a selected molecular size can be analyzed by the method of this disclosure to determine the ratio of ethylene to 1-octene of the copolymer of the selected molecular size.

The method of this disclosure could be scaled up to include large scale fractionations of many grams or many pounds of polymer by scaling up the size of the apparatus and the graphitic column.

In addition this disclosure could include a temperature gradient in addition to or instead of a solvent gradient as a way to perform the fractionation.

In addition this disclosure could include a fractionation in a commercial process to refine the purity of the comonomer distribution of the commercial product.

A preferred set of operating conditions for this disclosure are an EGMBE/TCB gradient with an autosampler and injector temperature of about 160° C. and a column temperature of about 140° C. Another preferred set of operating conditions for this disclosure are a decanol/TCB gradient with an autosampler, injector, and column temperature of about 175° C.

Example 1

Figure 3:
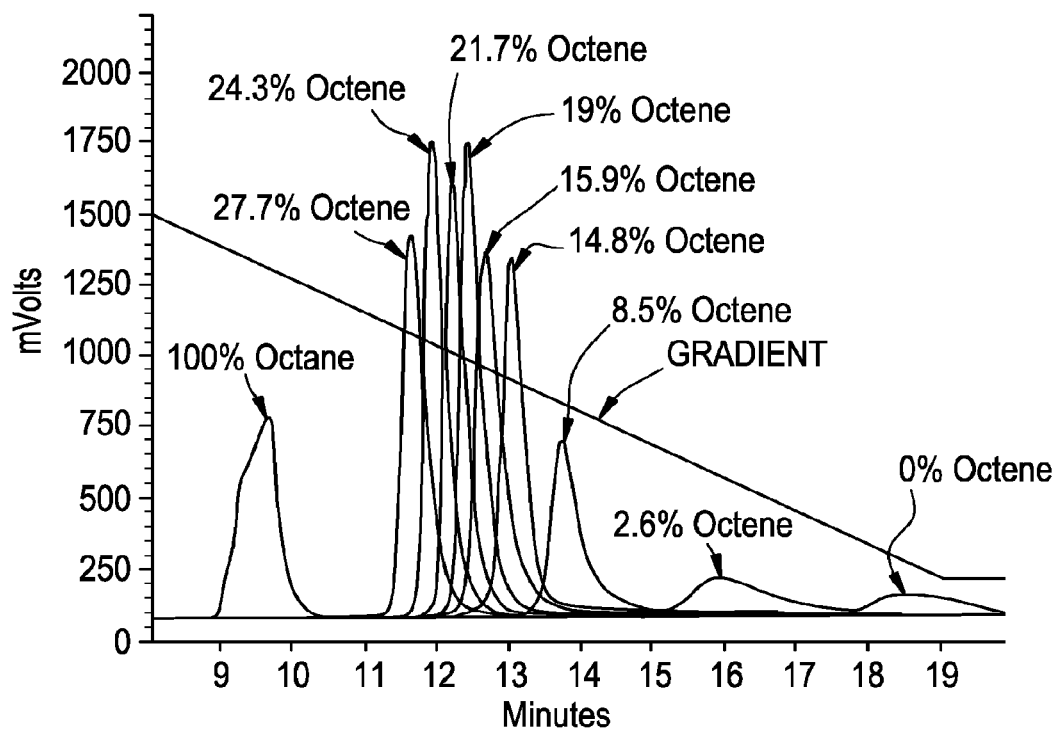
FIG. 3 is an overlay of chromatograms of polymers of 1-octene, ethylene and copolymers of various ratios of 1-octene and ethylene using a disclosed graphitic carbon stationary phase.
Figure 9A:
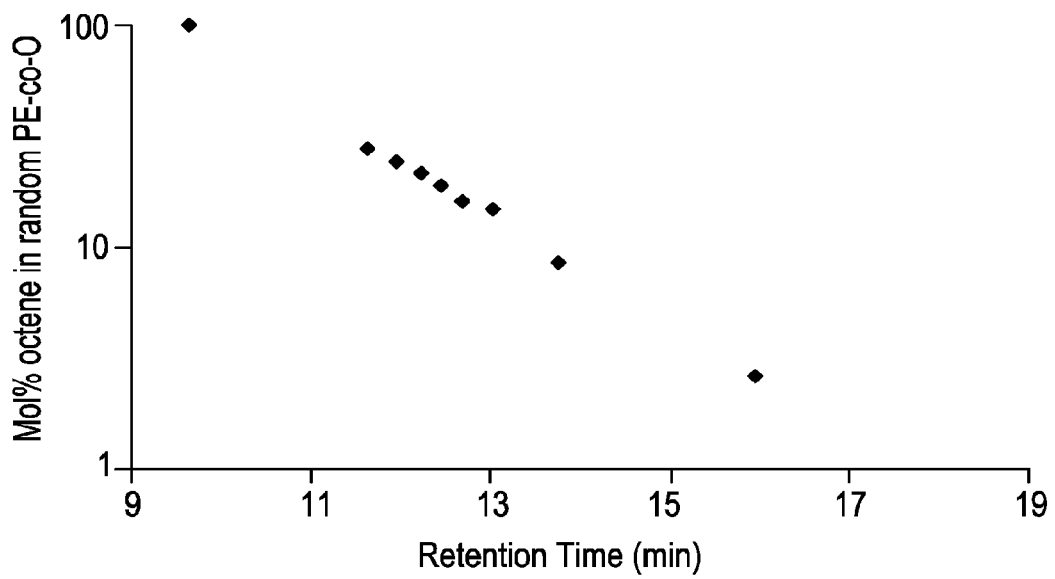
FIG. 9 is a calibration curve related to the chromatograms shown in FIG. 3.
Figure 9B:
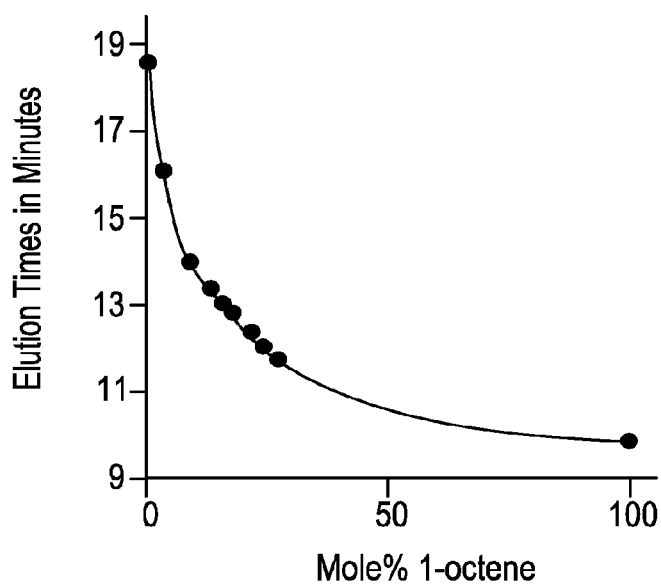

An HPLC system is assembled using a 4.6×100 mm, 5 micrometer packing size, 250 Å pore size, HYPERCARB brand liquid chromatography column, a gradient composition mobile phase at a flow rate of 1.0 milliliters per minute having an initial composition of 100 vol. % ethylene glycol mono butyl ether for 3 minutes after injection and then a 15 minute linear gradient composition change to 100 vol. % 1,2,4-trichloro benzene followed by a 3 minute hold at 100 vol. % 1,2,4-trichloro benzene, an injection volume of 10 micro liters, a sample concentration of 2 milligrams of polymer per milliliter of 160° C. decanol, a column temperature of 140° C., an injection valve temperature of 160° C., a Polymer Laboratories (Amherst, Mass.) ELS-1000 evaporative light scattering detector operated with a gas flow of 1.4 liters per minute, a nebulation temperature of 200° C. and an evaporation temperature of 250° C. Ten samples of copolymers of various mole ratios of polymerized ethylene and 1-octene monomers are prepared and chromatographed as shown in FIG. 3. The retention factors shown in FIG. 3 vary as a mathematical function of the monomer to comonomer ratio of the copolymer with 0 mole percent 1-octene (100 mole percent ethylene) having the highest retention factor and 100 mole percent 1-octene having the lowest retention factor. Such mathematical function can be expressed as the calibration curve shown in FIG. 9. Such mathematical function can be incorporated into the program of a general purpose digital computer to automatically determine the ratio.

Example 2

Figure 4:
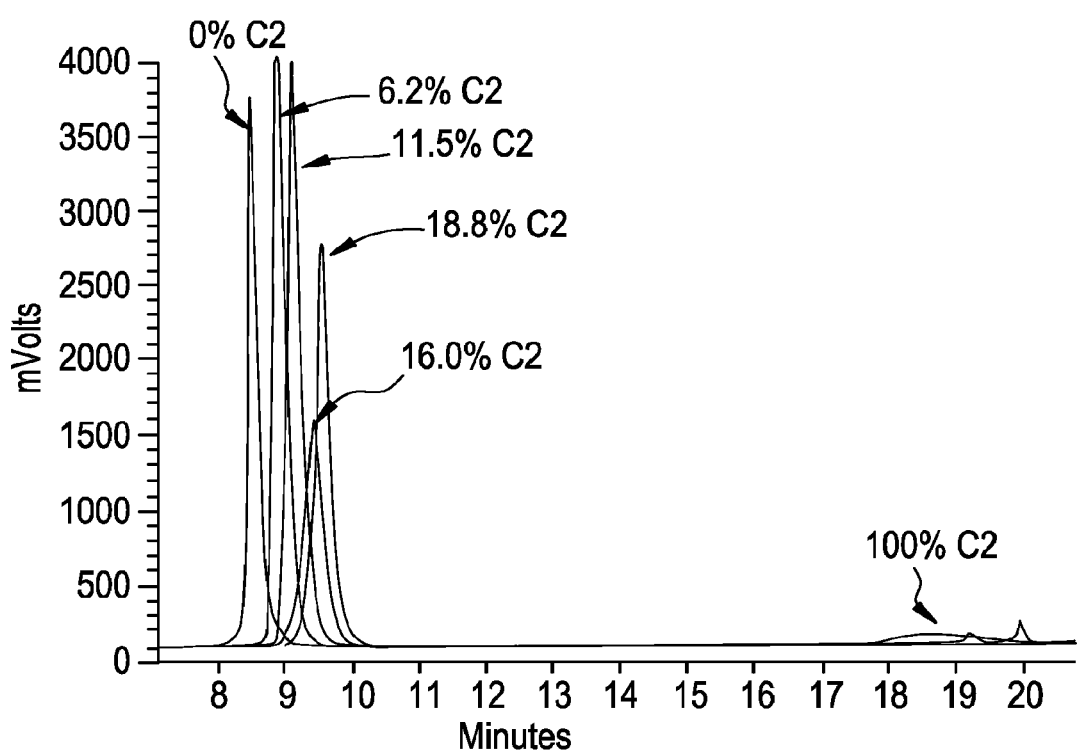
FIG. 4 is an overlay of chromatograms of polymers of propylene, ethylene and copolymers of various ratios of propylene and ethylene using a disclosed graphitic carbon stationary phase.

An HPLC system is assembled using a 4.6×100 mm, 5 micrometer packing size, 250 Å pore size, HYPERCARB brand liquid chromatography column, a gradient composition mobile phase at a flow rate of 1.0 milliliters per minute having an initial composition of 100 vol. % ethylene glycol mono butyl ether for 3 minutes after injection and then a 15 minute linear gradient composition change to 100 vol. % 1,2,4-trichloro benzene followed by a 3 minute hold at 100 vol. % 1,2,4-trichloro benzene, an injection volume of 10 micro liters, a sample concentration of 2 milligrams of polymer per milliliter of 160° C. decanol, a column temperature of 140° C., an injection valve temperature of 160° C., a Polymer Laboratories (Amherst, Mass.) ELS-1000 evaporative light scattering detector operated with a gas flow of 1.4 liters per minute, a nebulation temperature of 200° C. and an evaporation temperature of 250° C. Ten samples of copolymers of various mole ratios of polymerized ethylene and propylene monomers are prepared and chromatographed as shown in FIG. 4. The retention factors shown in FIG. 4 vary as a mathematical function of the monomer to comonomer ratio of the copolymer with 100 mole percent propylene (0 mole percent ethylene) having the lowest retention factor and 0 mole percent propylene (100 mole percent ethylene) having the highest retention factor.

Example 3

Figure 5:
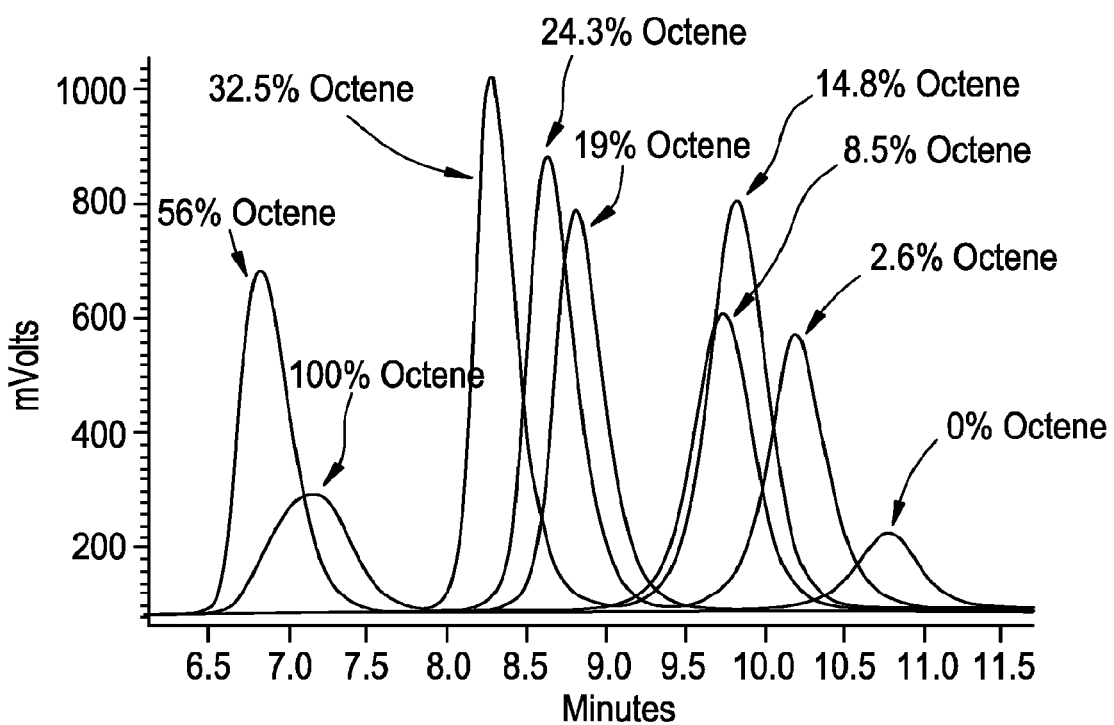
FIG. 5 is an overlay of chromatograms of polymers of 1-octene, ethylene and copolymers of various ratios of 1-octene and ethylene using a disclosed graphitic carbon stationary phase.

An HPLC system is assembled using a 4.6×50 mm, 5 micrometer packing size, DISCOVERY ZR-CARBON brand liquid chromatography column, a gradient composition mobile phase at a flow rate of 1.0 milliliters per minute having an initial composition of 100 vol. % ethylene glycol mono butyl ether for 3 minutes after injection and then a 15 minute linear gradient composition change to 100 vol. % 1,2,4-trichloro benzene followed by a 3 minute hold at 100 vol. % 1,2,4-trichloro benzene, an injection volume of 10 microliters, a sample concentration of 2 milligrams of polymer per milliliter of 160° C. decanol, a column temperature of 140° C., an injection valve temperature of 160° C., a Polymer Laboratories (Amherst, Mass.) ELS-1000 evaporative light scattering detector operated with a gas flow of 1.4 liters per minute, a nebulation temperature of 200° C. and an evaporation temperature of 250° C. Ten samples of copolymers of various mole ratios of polymerized ethylene and 1-octene monomers are prepared and chromatographed as shown in FIG. 5. The retention factors shown in FIG. 5 vary as a mathematical function of the monomer to comonomer ratio of the copolymer but with a functionality that is not as good as that shown in FIG. 3 because it appears that some samples having different ratios will have the same retention factor.

Example 4

Figure 6:
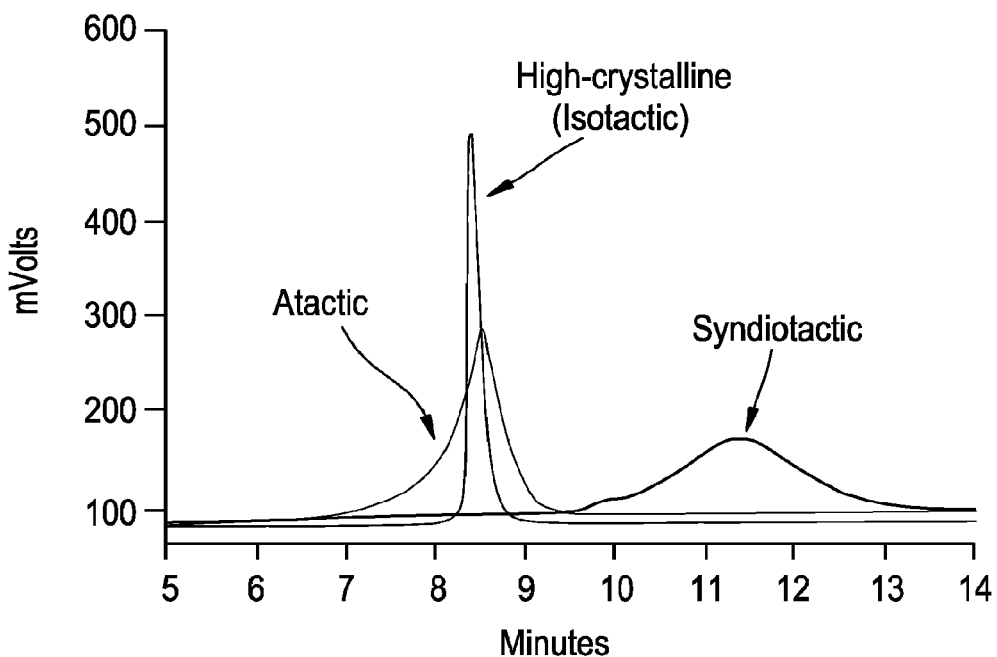
FIG. 6. is an overlay of three polypropylenes with different tacticities.

An HPLC system is assembled using a 4.6×100 mm, 5 micrometer packing size, 250 Å pore size, HYPERCARB brand liquid chromatography column, a gradient composition mobile phase at a flow rate of 1.0 milliliters per minute having an initial composition of 100 vol. % ethylene glycol mono butyl ether for 3 minutes after injection and then a 15 minute linear gradient composition change to 100 vol. % 1,2,4-trichloro benzene followed by a 3 minute hold at 100 vol. % 1,2,4-trichloro benzene, an injection volume of 10 micro liters, a sample concentration of 2 milligrams of polymer per milliliter of 160° C. decanol, a column temperature of 140° C., an injection valve temperature of 160° C., a Polymer Laboratories (Amherst, Mass.) ELS-1000 evaporative light scattering detector operated with a gas flow of 1.4 liters per minute, a nebulation temperature of 200° C. and an evaporation temperature of 250° C. Three samples of polypropylene of varying tacticity are prepared and chromatographed in FIG. 6 The retention of the polymers varies as a function of tacticity. Atactic and isotactic have a similar retention time, while syndiotactic is retained.

Comparative Example 1

Figure 7:
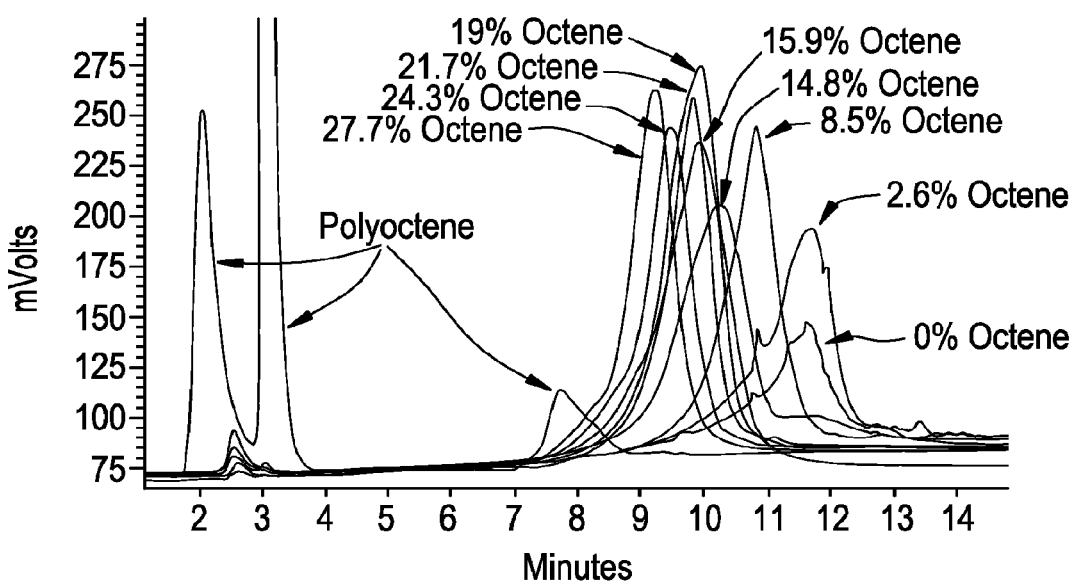
FIG. 7 is an overlay of chromatograms of polymers of 1-octene, ethylene and copolymers of various ratios of 1-octene and ethylene using a prior art silica stationary phase.

An HPLC system is assembled using a 4.6×250 mm, 5 micrometer packing size, 300 Å pore size Macherey Nagel silica liquid chromatography column (Macherey Nagel GmbH & Co. KG, Düren, Germany), a gradient composition mobile phase at a flow rate of 1.0 milliliters per minute having an initial composition of 100 vol. % ethylene glycol mono butyl ether for 3 minutes after injection and then a 15 minute linear gradient composition change to 100 vol. % 1,2,4-trichloro benzene followed by a 3 minute hold at 100 vol. % 1,2,4-trichloro benzene, an injection volume of 10 micro liters, a sample concentration of 2 milligrams of polymer per milliliter of 160° C. decanol, a column temperature of 140° C., an injection valve temperature of 160° C., a Polymer Laboratories (Amherst, Mass.) ELS-1000 evaporative light scattering detector operated with a gas flow of 1.4 liters per minute, a nebulation temperature of 200° C. and an evaporation temperature of 250° C. Ten samples of copolymers of various mole ratios of polymerized ethylene and 1-octene monomers are prepared and chromatographed as shown in FIG. 7. A comparison of the chromatograms shown in FIG. 7 with the chromatograms shown in FIG. 3 demonstrates the superior separation efficiency obtained using the graphitic carbon stationary phase of this disclosure in comparison to the use of a silica stationary phase of the prior art. In addition, artifact peaks are observed early in the chromatograms of FIG. 7 between 1.5 and 3.5 minutes, especially for the sample containing 100 mole percent 1-octene.

Comparative Example 2

Figure 8:
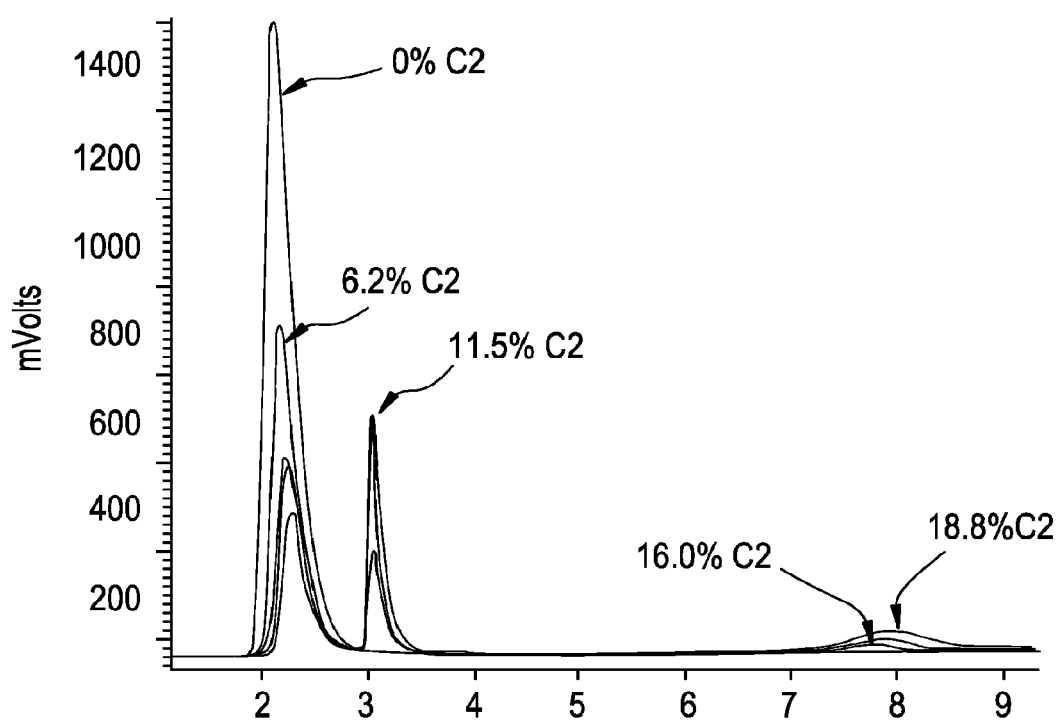
FIG. 8 is an overlay of chromatograms of polymers of propylene, ethylene and copolymers of various ratios of propylene and ethylene using a prior art silica stationary phase.

An HPLC system is assembled using a 4.6×250 mm, 5 micrometer packing size, 300 Å pore size Macherey Nagel silica liquid chromatography column (Macherey Nagel GmbH & Co. KG, Düren, Germany), a gradient composition mobile phase at a flow rate of 1.0 milliliters per minute having an initial composition of 100 vol. % ethylene glycol mono butyl ether for 3 minutes after injection and then a 15 minute linear gradient composition change to 100 vol. % 1,2,4-trichloro benzene followed by a 3 minute hold at 100 vol. % 1,2,4-trichloro benzene, an injection volume of 10 micro liters, a sample concentration of 2 milligrams of polymer per milliliter of 160° C. decanol, a column temperature of 140° C., an injection valve temperature of 160° C., a Polymer Laboratories (Amherst Mass.) ELS-1000 evaporative light scattering detector operated with a gas flow of 1.4 liters per minute, a nebulation temperature of 200° C. and an evaporation temperature of 250° C. Ten samples of copolymers of various mole ratios of polymerized ethylene and propylene monomers are prepared and chromatographed as shown in FIG. 8. A comparison of the chromatograms shown in FIG. 8 with the chromatograms shown in FIG. 4 demonstrates the superior separation efficiency obtained using the graphitic carbon stationary phase of this disclosure in comparison to the use of a silica stationary phase of the prior art.

What is claimed is:

1. A method for chromatography of a polyolefin polymer, comprising the following step: introducing a solution of the polyolefin polymer into a liquid flowing through a liquid chromatography stationary phase, the liquid chromatography stationary phase comprising graphitic carbon, and wherein the polyolefin polymer emerging from the liquid chromatography stationary phase has a retention factor greater than zero.

2. The method of claim 1, where the polyolefin polymer is a copolymer consisting essentially of ethylene and an alpha olefin.

3. The method of claim 2, where the alpha olefin consists essentially of 1-octene.

4. The method of claim 1, where the polyolefin polymer is a copolymer consisting essentially of propylene and an alpha olefin.

5. The method of claim 4, where the alpha olefin consists essentially of ethylene.

6. The method of claim 1, where the concentration of the polyolefin polymer in the solution of polyolefin polymer is greater than 0.1 milligrams per milliliter of solution.

7. The method of claim 1, where the liquid chromatography stationary phase consists essentially of graphitic carbon.

8. An improved liquid chromatography method comprising the step of introducing a solution of a polyolefin polymer into a liquid flowing through a liquid chromatography stationary phase, the polyolefin polymer emerging from the liquid chromatography stationary phase with a retention factor greater than zero, the improvement comprising the liquid chromatography stationary phase comprising graphitic carbon.

9. The method of claim 8, where the polyolefin polymer is a copolymer consisting essentially of ethylene and an alpha olefin.

10. The method of claim 9, where the alpha olefin consists essentially of 1-octene.

11. The method of claim 8, where the polyolefin polymer is a copolymer consisting essentially of propylene and an alpha olefin.

12. The method of claim 11, where the alpha olefin consists essentially of ethylene.

13. The method of claim 8, where the concentration of the polyolefin polymer in the solution of polyolefin polymer is greater than 0.1 milligrams per milliliter of solution.

14. The method of claim 8, where the liquid chromatography stationary phase consists essentially of graphitic carbon.

15. An apparatus for determining the monomer to comonomer ratio of a copolymer, wherein the apparatus comprises a high temperature liquid chromatography unit comprising a graphitic carbon liquid chromatography column, a pump, a polymer solution, and a means for an additional fractionation by size exclusion chromatography or asymmetric flow field flow fractionation, added after the fractionation by the graphitic column.

16. The apparatus of claim 15, wherein the apparatus further comprises a means to increase the temperature of the stationary phase within the column.

17. The apparatus of claim 15, wherein the apparatus further comprises a gradient composition mobile phase.

* * * * *